(12) United States Patent
Kühn et al.

(10) Patent No.: US 7,858,109 B2
(45) Date of Patent: Dec. 28, 2010

(54) IMPLANT MATERIAL

(75) Inventors: Klaus-Dieter Kühn, Marburg-Elnhausen (DE); Sebastian Vogt, Erfurt (DE)

(73) Assignee: Heraeus Kulzer GmbH, Hanau (DE)

( * ) Notice: Subject to any disclaimer, the term of this patent is extended or adjusted under 35 U.S.C. 154(b) by 583 days.

(21) Appl. No.: 11/675,127

(22) Filed: Feb. 15, 2007

(65) Prior Publication Data

US 2007/0190109 A1   Aug. 16, 2007

(30) Foreign Application Priority Data

Feb. 15, 2006   (DE) ................ 10 2006 007 245

(51) Int. Cl.
*A61F 2/00* (2006.01)
*A61K 31/70* (2006.01)
*A61K 38/16* (2006.01)
*A61K 31/496* (2006.01)

(52) U.S. Cl. .................. 424/423; 514/8; 514/35; 514/37; 514/39; 514/253.08

(58) Field of Classification Search .......... 424/423
See application file for complete search history.

(56) References Cited

U.S. PATENT DOCUMENTS

| | | | | |
|---|---|---|---|---|
| 5,756,127 A * | 5/1998 | Grisoni et al. | ............ | 424/489 |
| 7,030,093 B2 * | 4/2006 | Vogt et al. | ............ | 514/25 |
| 2003/0004491 A1 * | 1/2003 | Tenhuisen et al. | ............ | 604/502 |
| 2006/0035376 A1 * | 2/2006 | Geltser | ............ | 435/395 |

FOREIGN PATENT DOCUMENTS

DE   26 51 441 A1   5/1978
DE   30 37 2701 A1   5/1982

OTHER PUBLICATIONS

Resorbable Antibiotic Coatings for Bone Substitutes and Implantable Devices. Vogt et al. (submitted in IDS).*
Antibiotic-Impregnated Heart Valve Sewing Rings for Treatment and Prophylaxis of Bacterial Endocarditis. Cimbollek et al. (submitted in IDS).*
S. Vogt, Resorbable Antibiotic Coatings for Bone Substitutes and Implantable Devices, 2005, pp. 814-819.

* cited by examiner

*Primary Examiner*—Shanon A Foley
*Assistant Examiner*—Sarah Al-Awadi
(74) *Attorney, Agent, or Firm*—Norris McLaughlin & Marcus, P.A.

(57) ABSTRACT

Form bodies, which can be rotationally-symmetrical or irregularly-shaped, consist of at least one member of the group of the antibiotic salts, gentamicin myristate, gentamicin palmitate, gentamicin stearate, tobramycin myristate, tobramycin palmitate, tobramycin stearate, amikacin myristate, amikacin palmitate, amikacin stearate, vancomycin palmitate, vancomycin stearate, ramoplanin palmitate, ramoplanin stearate, levofloxacin palmitate, levofloxacin stearate, ofloxacin palmitate, ofloxacin stearate, moxifloxacin palmitate, moxifloxacin stearate, clindamycin palmitate, and clindamycin stearate. A medical device for implantation, in which the form bodies are arranged on a biodegradable filament at a distance of 1 mm to 25 mm as well as a method for the manufacture of the medical device and the use of the form bodies or the medical device to treat chronic osteomyelitis are described.

8 Claims, No Drawings

IMPLANT MATERIAL

The present invention relates in one embodiment to a biodegradable implant material designed to serve as a local antibiotic reservoir during the treatment of chronic osteomyelitis.

To date, one of the most difficult challenges of bone surgery continues to be the treatment of osteomyelitis. Osteomyelitis can have a hematogenous, posttraumatic or postoperative aetiology. Particularly difficult is the chronic form of osteomyelitis which can lead to a loss of limbs and even sepsis in extreme cases. Commonly, the treatment of chronic osteomyelitis involves surgical management by means of radical debridement. This involves extensive removal of the infected or necrotic bone. Subsequently, the bone cavity is filled with a local antibiotic carrier or treated by means of suction-irrigation drainage. Local release of large quantities of antibiotic from an antibiotic carrier is effective against any bacterial pathogens remaining in the adjacent bone areas provided a sufficiently bone-permeable bactericidal antibiotic, such as gentamycin sulfate, is used.

Approximately-sphere-shaped-local agent release systems made of polymethylmethacrylate, zirconium dioxide and a conventional water-soluble antibiotic, such as gentamycin sulfate, were first described in 1975 by Klaus Klemm (DE 23 20 373). This concept proved successful, but was also disadvantageous in that only a small fraction of the agent contained in the spheres was actually released.

As a further development of these agent carriers, Heuser and Dingeldein proposed in 1978 to add glycine or other amino acids to improve the release of antibiotic (DE 26 51 441). Upon exposure to blood or exudations from a wound, the incorporated amino acids dissolve and form pore systems from which the agent can diffuse. This achieved improved release of the agent. Agent carriers designed according to this principle are currently on the market in the form of the pearl string-shaped Septopal® chains. In these, the agent carriers have been sprayed onto a polyphilic steel wire. The retarded release is based on diffusion of the agent from the polymer matrix. The essential disadvantage of the Septopal® chains is that the chains generally need to be removed after approx. 10 days. This necessitates a second intervention which is associated with additional inconvenience for the patient and causes additional costs.

In the following, it was aimed to develop a completely biodegradable, pearl string-shaped local agent release system in order to avoid the need for a second intervention to remove the agent release system.

Accordingly, DE 30 37 270 described an agent carrier that consists essentially of a biodegradable filament on which form bodies made of fibrin are arranged. An antibiotic is incorporated in the fibrin form bodies.

U.S. Pat. No. 5,756,127 proposed a pearl string-shaped agent carrier, in which form bodies made of calcium sulfate are attached on a biodegradable filament. In this context, the calcium sulfate serves as matrix for the agent. However, it must be critically noted that the implantation of major quantities of calcium sulfate has occasionally been observed to be associated with seroma formation.

DE 102 27 935 only describes porous bodies coated with antibiotic-fatty acid salts.

DE 101 14 244 AI relates to mixtures consisting of easily water-soluble antibiotic salts and salts of amphiphilic substances (e.g. alkylsulfonates), which, in combination with excipients, are shaped into form bodies and can directly serve as implants with antibiotic efficacy. In this context, it is essential that sparingly water-soluble antibiotic salts form in situ within the implants by reciprocal-salt exchange only upon contact with water or body fluid.

DE 101 14 364 AI describes the use of antibiotic-fatty acid salts, antibiotic-organosulfates or antibiotic-organosulfonates, as binding agents for the manufacture of form bodies containing organic or inorganic excipients.

In summary, it can be concluded that the basic principle of the agent release systems proposed in the patents, DE 23 20 373, DE 26 51 441, DE 30 37 270, and U.S. Pat. No. 5,756,127, is that the agent is incorporated in a matrix from which the agent is slowly released by dissolution due to the effect of blood or exudations from a wound. The agent release systems mentioned are disadvantageous in that there is always a matrix present which can either be manufactured only with considerable difficulty or which, due to its composition, can elicit adverse side effects during its absorption and because of the degradation products generated therefrom.

An object of the present invention was to develop an implant material that is suitable for use as a locally applicable antibiotic reservoir for the treatment of osteomyelitis. The implant material is intended to overcome the disadvantages of the known gentamicin-containing pearl string-shaped agent release systems.

This object of the invention is met by an implant material made from rotationally symmetrical or irregularly shaped form bodies that are formed from at least one representative of the sparingly water-soluble antibiotic salts, gentamicin myristate, gentamicin palmitate, gentamicin stearate, tobramycin myristate, tobramycin palmitate, tobramycin stearate, amikacin myristate, amikacin palmitate, amikacin stearate, vancomycin palmitate, vancomycin stearate, ramoplanin palmitate, ramoplanin stearate, levofloxacin palmitate, levofloxacin stearate, ofloxacin palmitate, ofloxacin stearate, moxifloxacin palmitate, moxifloxacin stearate, clindamycin palmitate, and clindamycin stearate. The terms, palmitate, stearate, and myristate, shall be understood to refer to the antibiotic salts of palmitic acid, stearic acid, and myristic acid, respectively. In this context, the preferred ratio of protonated amino acid and fatty acid anion is equal to 1. However, it is also feasible for only a fraction of the protonated amino acids to have fatty acid anions as counter-ions. Accordingly, for example, gentamicin pentakispalmitate, gentamicin tetrakispalmitate or gentamicin tripalmitate can be used as sparingly water-soluble antibiotic salts.

This object was further met according to the invention by a medical device for implantation, in which the rotationally symmetrical and/or irregularly shaped form bodies described above are arranged on a biodegradable filament at distance of 1 mm to 25-mm. A medical-device of-this type that has 10, 20 or 30 form bodies arranged along the filament axis is preferred. Basically, any absorbable filament material is suitable for use as filaments. Surprisingly, the sparingly water-soluble antibiotic salts mentioned above can be shaped into sufficiently stable form bodies without the additional use of matrix-forming substances. Although it is feasible to provide excipients, there is no requirement to have conventional inorganic or organic matrix-forming excipients present. Such excipients would be, e.g., palmitic acid, myristic acid, stearic acid, glycerol tripalmitate, glycerol trimyristate or glycerol tristearate, whereby the excipient content commonly can account for up to 90 weight percent.

In another embodiment, the present invention also relates to a method for the manufacture of a device corresponding to the one described in the preceding paragraph. In this context, the sparingly water-soluble salts are pressed onto the filament in known fashion and then heat-treated at 50-70° C.

Sphere-shaped form bodies made of gentamicin palmitate (activity coefficient of 251) having a mass of 30 mg each (equivalent to 7.5 mg gentamicin base per form body) that are arranged at a distance of 10 mm each along the filament axis to prevent overdosing have proven particularly useful. The particular advantage of this implant material is that the form bodies consisting of one or more sparingly water-soluble antibiotic salts dissolve parallel to the release of the agent and in that the individual form bodies are kept at a distance from each other by the filament. This renders the possibility of overdosing much more difficult. The pearl string-shaped arrangement allows for the filling of larger bone cavities with a relatively small number of form bodies. An essential advantage of the implant material according to the invention is that no matrix-forming substances are required. This precludes problems related to any degradation products. Another advantage of the implant material is the use of antibiotic salts containing even-numbered fatty acids. The even-numbered fatty acids, such as palmitic acid and stearic acid, are natural components of the human organism and are metabolized by β-oxidation without any difficulty.

Preferably, the biodegradable filament is braided. The form bodies adhere particularly well to braided polyglycolide filaments.

Although it is feasible to add easily water-soluble antibiotics to the form bodies, it is preferred according to the invention for these not to be contained therein. Easily water-soluble antibiotics are, for example, gentamicin sulfate, tobramycin sulfate, amikacin sulfate, levofloxacin hydrochloride, ofloxacin hydrochloride, moxifloxacin hydrochloride, and clindamycin-hydrochloride. The incorporation of easily water-soluble antibiotics usually is associated with the advantage of a high initial release of agent in the first hours after insertion of the implant material into an aqueous environment. It is feasible to add further water-soluble antiinfective agents serving the same purpose.

According to one embodiment of the present invention, a pearl string-shaped implant material that does not require a matrix is provided.

The invention is illustrated in more detail by the following non-limiting examples:

EXAMPLE 1

A conventional tabletting machine is used to manufacture from gentamicin palmitate powder (activity coefficient of 251) oblong form bodies with a mass of 35 mg (equivalent to 8.8 mg gentamicin base). Two form bodies are removed for determining gentamicin release and stored in 20 ml phosphate buffer pH 7.4 at 37° C. Fifteen ml release medium are withdrawn daily for determining the gentamicin content and replaced by 15 ml fresh phosphate buffer. A TDX Analyser made by Abbott is used to determine the gentamicin content. The results are shown in Table 1.

EXAMPLE 2

A special-made tabletting machine is used to press oblong form bodies with a mass of 30 mg (equivalent to 7.5 mg gentamicin base) made from gentamicin palmitate powder (activity coefficient of 251) onto a braided polyglycolide filament at a distance of 10-11 mm each. Two form bodies are cut out for determining gentamicin release and stored in 20 ml phosphate buffer pH 7.4 at 37° C. Fifteen ml release medium are withdrawn daily for determining the gentamicin content and replaced by 15 ml fresh phosphate buffer. A TDX Analyser made by Abbott is used to determine the gentamicin content. The results are shown in Table 1.

| Cumulative release of gentamicin base [μg/form body] | | | | | | | |
|---|---|---|---|---|---|---|---|
| Time [d] | | | | | | | |
| 1 | 2 | 3 | 4 | 7 | 8 | 9 | 10 |
| Form body Example 1: 1192 | 1759 | 2375 | 3641 | 3974 | 4294 | 4550 | 4773 |
| Form body Example 2: 1101 | 1696 | 2315 | 3581 | 3920 | 4255 | 4504 | 4760 |

What is claimed is:

1. Biodegradable filament having arranged thereon pressed form bodies consisting of:
   (i) at least one member of the group of the antibiotic salts, gentamicin myristate, gentamicin palmitate, gentamicin stearate, tobramycin myristate, tobramycin palmitate, tobramycin stearate, amikacin myristate, amikacin palmitate, amikacin stearate, vancomycin palmitate, vancomycin stearate, ramoplanin palmitate, ramoplanin stearate, levofloxacin palmitate, levofloxacin stearate, ofloxacin palmitate, ofloxacin stearate, moxifloxacin palmitate, moxifloxacin stearate, clindamycin palmitate, and clindamycin stearate; and, optionally,
   (ii) at least one water-soluble antibiotic.

2. The biodegradable filament according to claim 1, wherein the pressed form bodies are irregular in shape.

3. The biodegradable filament according to claim 1, wherein the pressed form bodies have a rotationally-symmetrical shape.

4. Medical device for implantation, comprising the biodegradable filament according to claim 1, wherein the form bodies are arranged on the biodegradable filament at a distance of 1 mm to 25 mm.

5. The medical device according to claim 4, wherein the biodegradable filament is braided.

6. Method for manufacturing a device according to claim 4, comprising pressing form bodies of at least one antibiotic salt onto a filament and subsequently heat-treating at 50-70° C., wherein the at least one antibiotic salt is at least one member selected from the group consisting of the antibiotic salts, gentamicin myristate, gentamicin palmitate, gentamicin stearate, tobramycin myristate, tobramycin palmitate, tobramycin stearate, amikacin myristate, amikacin palmitate, amikacin stearate, vancomycin palmitate, vancomycin stearate, ramoplanin palmitate, ramoplanin stearate, levofloxacin palmitate, levofloxacin stearate, ofloxacin palmitate, ofloxacin stearate, moxifloxacin palmitate, moxifloxacin stearate, clindamycin palmitate, and clindamycin stearate.

7. A method of treating chronic osteomyelitis in a patient in need of such treatment, comprising implanting into said patient form bodies according to claim 1.

8. A method of treating chronic osteomyelitis in a patient in need of such treatment, comprising implanting into said patient a device according to claim 4.

* * * * *